United States Patent
Enpuku

(10) Patent No.: US 6,770,489 B1
(45) Date of Patent: Aug. 3, 2004

(54) METHOD FOR AN IMMUNOASSAY WITH A MAGNETIC LABEL AND AN APPARATUS FOR THE SAME

(75) Inventor: Keiji Enpuku, Fukuoka (JP)

(73) Assignee: Sumitomo Electric Industries, Ltd., Osaka (JP)

( * ) Notice: Subject to any disclaimer, the term of this patent is extended or adjusted under 35 U.S.C. 154(b) by 0 days.

(21) Appl. No.: 09/621,341

(22) Filed: Jul. 21, 2000

(30) Foreign Application Priority Data

Jul. 21, 1999 (JP) .......................................... 11-206248

(51) Int. Cl.[7] .............................................. G01N 33/553
(52) U.S. Cl. ....................... 436/526; 436/501; 436/518; 436/517; 436/535; 436/514; 436/538; 422/68.1
(58) Field of Search ................. 436/501, 514, 436/517, 526, 518, 535, 538, 806; 422/68.1

(56) References Cited

U.S. PATENT DOCUMENTS

| | | | |
|---|---|---|---|
| 5,318,914 A | * | 6/1994 | Matte et al. |
| 5,496,534 A | * | 3/1996 | Klaveness et al. |
| 5,981,297 A | * | 11/1999 | Baselt |
| 6,027,946 A | * | 2/2000 | Weitschies et al. |
| 6,084,399 A | * | 7/2000 | Nagaishi et al. |
| 6,123,902 A | * | 9/2000 | Koch et al. |
| 6,238,899 B1 | * | 5/2001 | Blackman et al. |
| 6,275,031 B1 | * | 8/2001 | Simmonds |
| 6,307,372 B1 | * | 10/2001 | Sugarman et al. |

FOREIGN PATENT DOCUMENTS

JP 630090765 A * 4/1988 .......... G01N/33/54

* cited by examiner

Primary Examiner—Christopher L. Chin
Assistant Examiner—Pensee T. Do
(74) Attorney, Agent, or Firm—Foley & Lardner LLP

(57) ABSTRACT

The present invention relates to an immunoassay and an apparatus for the same. A method of the present invention comprises following processes: (1) an analyte is labeled to detect antigen-antibody reaction, (2) the magnetic material label is magnetized by a magnetic field, (3) the magnetized magnetic material label detected by a SQUID which detect a magnetic field having right angle to the magnetic field. At the same time, the present invention contains an apparatus to execute the method provided by the present invention. The apparatus comprises a magnetic field generation means that generates a magnetic field to magnetize the labels. The apparatus comprises a SQUID that measures magnetic field.

11 Claims, 6 Drawing Sheets

● AType
□ BType

METHOD FOR AN IMMUNOASSAY WITH A MAGNETIC LABEL AND AN APPARATUS FOR THE SAME

DETAILED DESCRIPTION OF THE INVENTION

1. Field of the Invention

The present invention relates to an immnunoassay and an apparatus for the same. More specifically, the present invention relates to a method and an apparatus for an immunoassay with a magnetic label and a SQUID.

2. Detailed Description of Invention

An immunoassay is a method to detect an antigen or an antibody (mentioned with the word "analyte" in this specification). For identification or measurement, a label is attached to antibody of an antigen-antibody reaction. Various labels and detection method have been proposed and are frequently used.

In particular, various optical methods are well known. In these methods, labels with light, fluorescence or color are used. However, optical methods have too short a sensitivity time for many applications.

As another method, a method using radioactive label is known. However, this method has problems concerning safety which limit its applicability.

Furthermore, there is methods with magnetic labels as a reemergence measurement or a magnetic relaxation method. However, in this method, grain size of the label influences the measured value seriously. Therefore, accuracy of measurement of this method is not stable.

On the other hand, a SQUID has recently been put to practical use. The SQUID comprises a circular current load and one or two Josephson junction(s) on the load. The SQUID has a very high sensitivity compared with a Hall device or a flux gate and is used as a magnetism sensor.

A new assessment method with magnetic label has been developed in accordance with the invention. In this method, it is expected that labels can be detected by a SQUID with high accuracy. However, there is no known practical method to use a SQUID in this context. Magnetic labels have to be magnetized for detection by a SQUID. However, a strong magnetic field of dozens of gauss is necessary for the label to be magnetized.

On the other hand, a SQUID has a very high sensitivity. Therefore, a serious problem occurs in that a SQUID receives the effects of the magnetic field of magnetization means and the desired measured value of the label changes.

Furthermore, an analyte is actually treated with a prepared slide. But, a strong magnetic field magnetizes the prepared slide. Therefore, it is difficult to detect only a label.

SUMMARY OF THE INVENTION

The present invention provides a method for an immunoassay with magnetized label and SQUID, which comprising following processes;

(1) an analyte is labeled with a magnetic material label to detect antigen-antibody reaction,
(2) the magnetic material label is magnetized by a magnetic field,
(3) the magnetized magnetic material label detected by a SQUID which detect a magnetic field having right angle to the magnetic field.

In method of the present invention, labels are magnetized and detected by a SQUID. According to a preferable embodiment of the present invention, the magnetic field for magnetization is a static magnetic field.

According to another preferable embodiment of the present invention, an analyte is inspected while moving parallel to the flux forming the magnetic field inside the detection region of the SQUID. Then, the SQUID detects a variation of magnetic field occurred by the moving labels magnetized in particular direction.

At the same time, the present invention contains an apparatus to execute the method provided by the present invention. The apparatus comprises a magnetic field generation means that generates a magnetic field to magnetize the labels. The apparatus comprises a SQUID that measures the magnetic field.

It is preferable that the apparatus comprises a trsportation means which moves the analyte with the magnetized label parallel to the magnetic field generated by the magnetic field generation means.

Furthermore, the apparatus preferably comprises magnetic field compensation means. The compensation means generates a magnetic field parallel to the detection direction of the SQUID. The magnetic field for compensation cancels the magnetic field is at a right angle to the magnetic field for magnetization. Because, the magnetic field for magnetization contains a component that has a right angle to the desired magnetic field and the SQUID has very high sensitivity to detect the component.

According to the preferable embodiment of the present invention, the SQUID is formed of an oxide superconducting thin film having a high critical temperature. By the way, the sensitivity of a SQUID is proportional to the third power of the distance between the SQUID and the analyte. The oxide superconducting materials can be used with a small cooling-systems. The use of the oxide superconducting materials is advantageous in this point.

It is an important characteristic of the present invention that the magnetic field for magnetization is at a right angle to the magnetic field detected by the SQUID. That is to say, in a prior art, the magnetic field for magnetization and the magnetic field detected are parallel to each other. Therefore, the SQUID also detects the magnetic field for magnetization.

On the contrary, in apparatus of the present invention, the magnetic fields are arranged at right angles to each other. The SQUID detects a flux at a right angle to its circular current load and never detects a flux parallel to the circular current load. Therefore, in an apparatus provided by the present invention, the SQUID does not detect the magnetic field for magnetization. In a method using a SQUID of the prior art, a magnetic field for magnetization is an alternative and a noise is offset by using a lock in amplifier.

According to a preferable embodiment of the present invention, a static magnetic field can be used. Because, the static magnetic field can be easily compensated by simple means with a solenoid.

However, because the SQUID has very high sensitivity, even using the magnetic field for compensation will not compensate the magnetic field for magnetization perfectly. Then, according to a preferable embodiment of the present invention, the SQUID detects a variation of the magnetic field. This variation of magnetic field occurs because of motion of the magnetized label in the detection field. This variation itself is not influenced by the magnetic field of the perimeter.

The above and other objects, features and advantages of the present invention will be apparent from following description of preferred embodiments of the invention with reference to the accompanying drawings.

DESCRIPTION OF THE PREFERRED EMBODIMENTS

Figure 1:
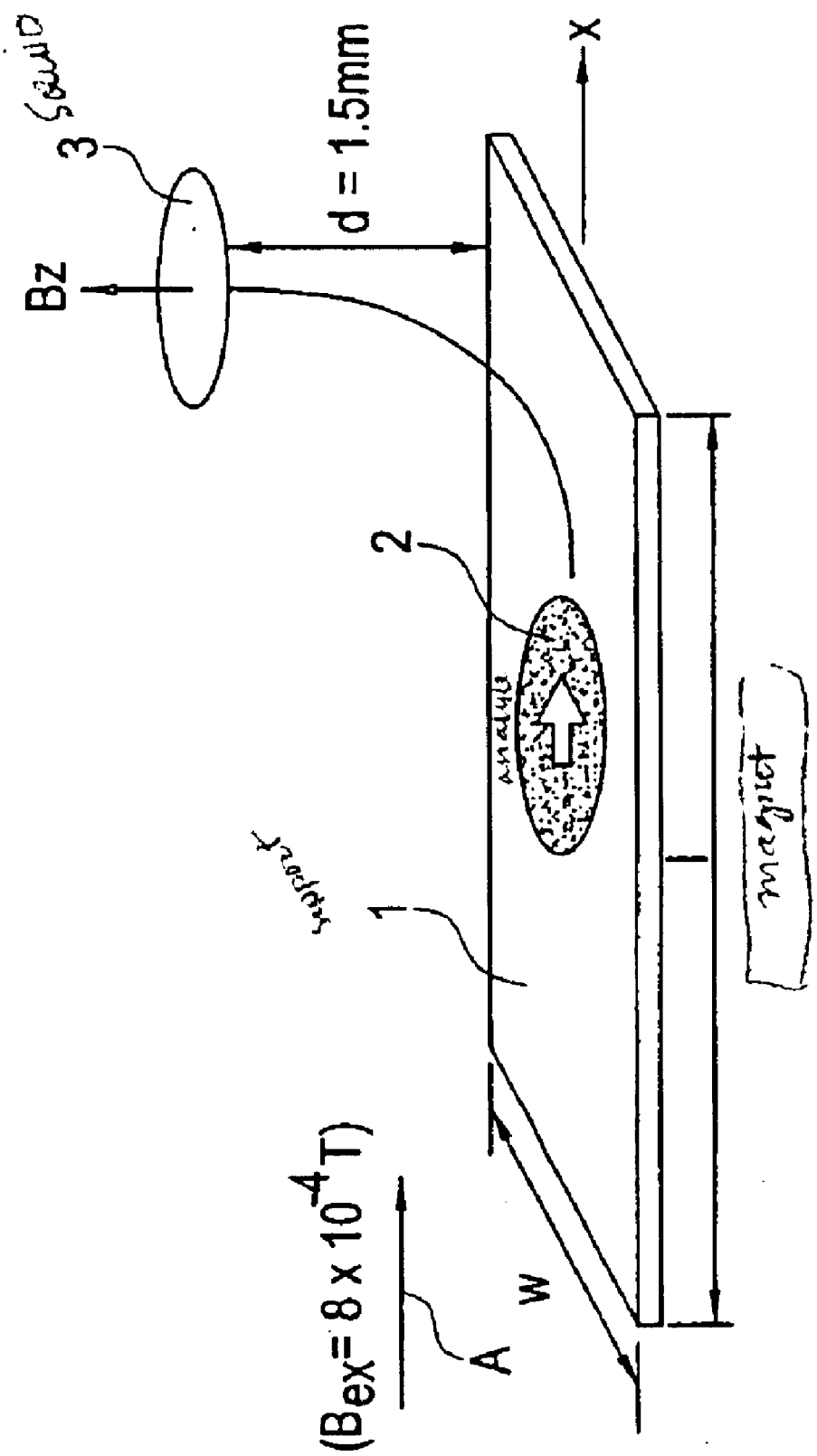
FIG. 1 is a perspective view showing a principle of the method provided by the present invention.

In the method of the present invention, as shown in the FIG. 1, an analyte 2 supported on a support 1 with label is magnetized at first by a magnetic field shown with arrow A parallel to surface of the support 1, and is detected by a SQUID 3.

The SQUID 3 comprises a ringed current load that is arranged parallel to the surface of the support 1. Therefore, a magnetic flux detected by the SQUID 3 is at a right angle to the surface of the support 1. Namely, a region under the SQUID 3 becomes a detection region of the SQUID 3. On the contrary, the magnetic field for magnetization is parallel to the surface of the support 1. Therefore, the SQUID 3 has substantially no sensitivity to the magnetic field A for magnetization.

Furthermore, the support 1 moves parallel to the magnetic field A with fixed velocity X. When the analyte 2 passes into the detection region of the SQUID 3, the magnetic field of the detection region changes and the SQUID 3 detects the change of the magnetic field. By the way, at the same time, the support 1 is magnetized too. Therefore, it is preferable that the length L and the width W of support 1 are sufficiently large so that the detection region is initially met by support 1 while no analyte 2 is in the detection region.

Figure 2:
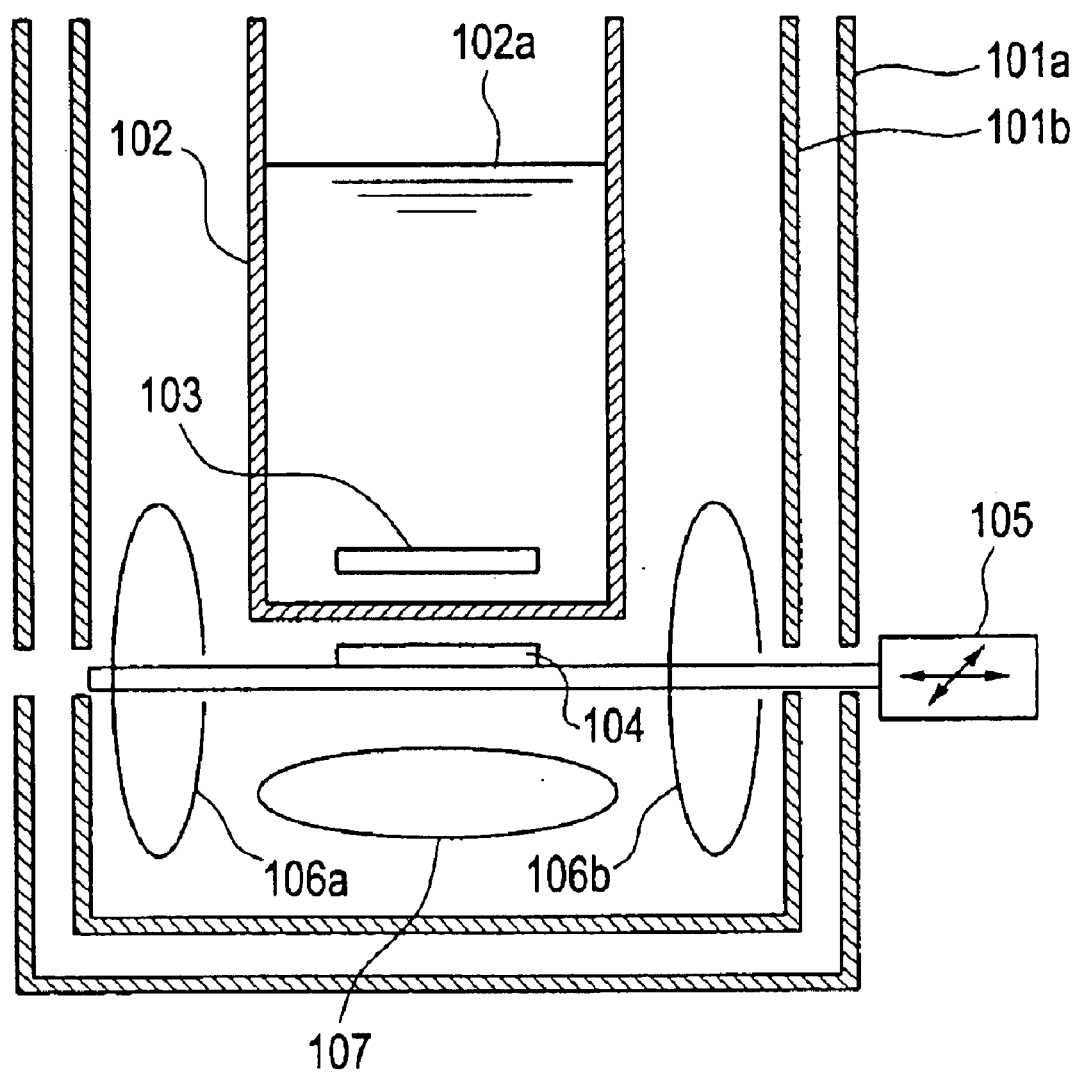
FIG. 2 is a sectional view showing a basic construction of the apparatus provided by the present invention.

The method mentioned above can be executed with an apparatus shown by FIG. 2. This apparatus comprises magnetic shields 101a, 101b, SQUID 103, coils for magnetization 106a, 106b, a compensating coil 107 and a transportation means 105.

The magnetic shields 101a, 101b surround the whole apparatus and the measurement is done within the magnetic shields 101a, 101b. SQUID 103 is taken into a container 102 filled with liquid nitrogen 102a and arranged horizontally. The magnetization coils 106a, 106b are placed parallel mutually and have right angle to the SQUID 103.

The compensating coil 107 is placed in the lower part of the SQUID 103 and arranged parallel to the SQUID 103. Any vertical component of the magnetic field generated by the magnetization coils 106a, 106b is canceled with the magnetic field formed by the compensating coil 107. Then the magnetic field inside the detection region includes substantially only horizontal flux.

The transportation means 105 comprises an arm that moves to X-Y direction in horizontal and conveys a sample 104. Transportation means 105 can carry sample 104. The sample 104 is inserted into the magnetic shields 101a, 101b from the side by the transportation means 105 and passes inside the coil 106a, 106b. Then the sample 104 is magnetized by the coil 106a, 106b. Next, the sample 104 arrives the detection region.

We assembled the apparatus mentioned above with elements below.

The SQUID 103 was made of patronized oxide superconducting thin film on a $SrTiO_3$ substrate. The magnetic shields 101a, 101b were made of Permalloy.

Sample 104 was supported by a glass plate having dimension of 20 mm*80 mm as a support 1. The glass plate is produced by Nalge Numc International company (USA). The glass plate passed 1.5 mm lower part of the SQUID.

We prepared two kinds of antibody for preparation samples.

Figure 3A:
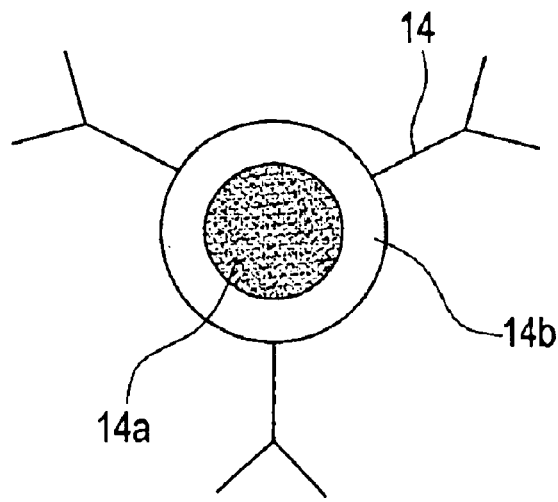
FIG. 3 shows labels and antibodies.

One is a A type antibody named "MACS" provided from Miltenyi Biotec company (Germany). The MACS is a particle of gamma-$Fe_2O_3$ 14a coated by a polymer 14b and antibody 14 sticks to the polymer 1.4b as shown in FIG. 3 (a). Average particle diameter of the A type antibody is 50 nm and weight of A type antibody is approximately $4*10^{-16}$ g.

Figure 3B:
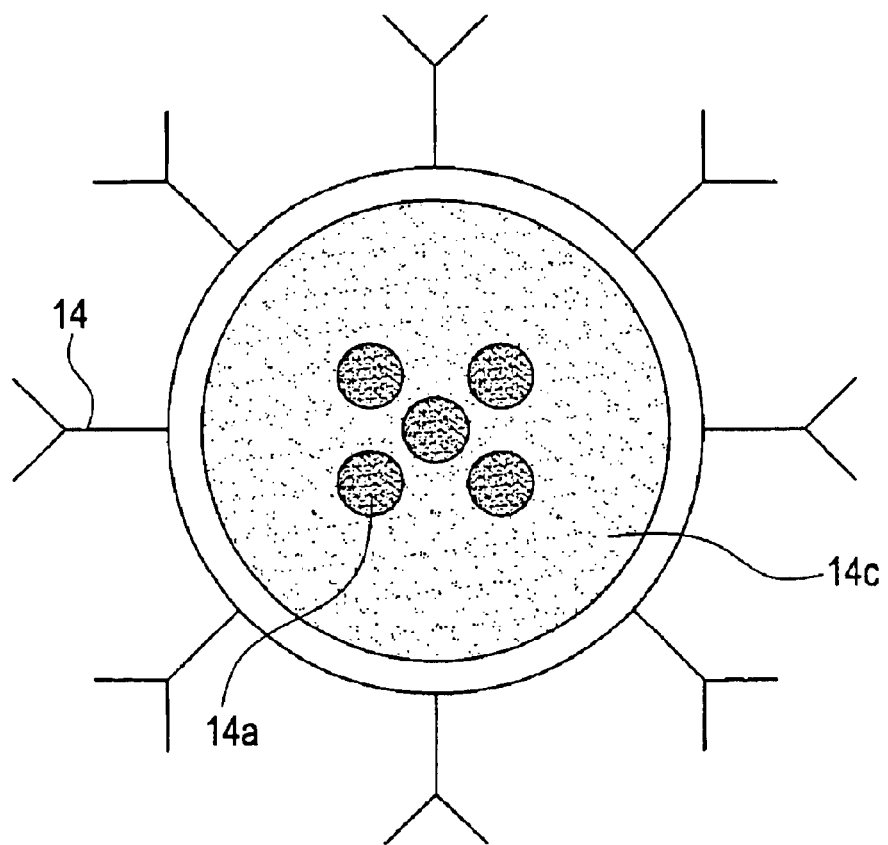

Another one is a B type antibody named "dynabeads" provided by Dynal company (Norway). Plural magnetic material ultrafine particle 14a is contained in a polymer graining 14c as shown in figure 3(b) and an antibody 14 sticks to polymer 14c. Average particle diameter of B type antibody is 4.5 μm and weight of B type antibody is approximately $14.3*10^{-12}$ g.

EXAMPLE 1

Sample mentioned above was inspected with apparatus shown by FIG. 2. We used a decentralized liquid of A type antibody (rat/anti mouse Ig GI). In stock solution, concentration was indicated 0.2 mg/ml and Average particle diameter was 50 nm, 5.2 g/cm³. According to the inference, weight of magnetic material particle is $3.4*10^{-16}$ g and the particle is contained during stock solution at $5.8*10^{11}$/ml. Then we diluted the stock solution with PBS into 1/10 and put it on the glass plate as an analyte. The sample on the glass plate occupied a region with 2 mm diameter and its amount was 2 μliter. Accordingly, this sample contains $1.2*10^8$ magnetic particles and general mass of the magnetic particles is 40 ng.

The acidity of magnetic field for magnetization was $8*10^{-4}$ T and the drift speed of analyte was 8 mm per second. Output signal of the SQUID 103 was recorded through a band-pass filter having range from 0.1 Hz to 5 Hz. Recorded output signal is shown in FIG. 4.

Figure 4:
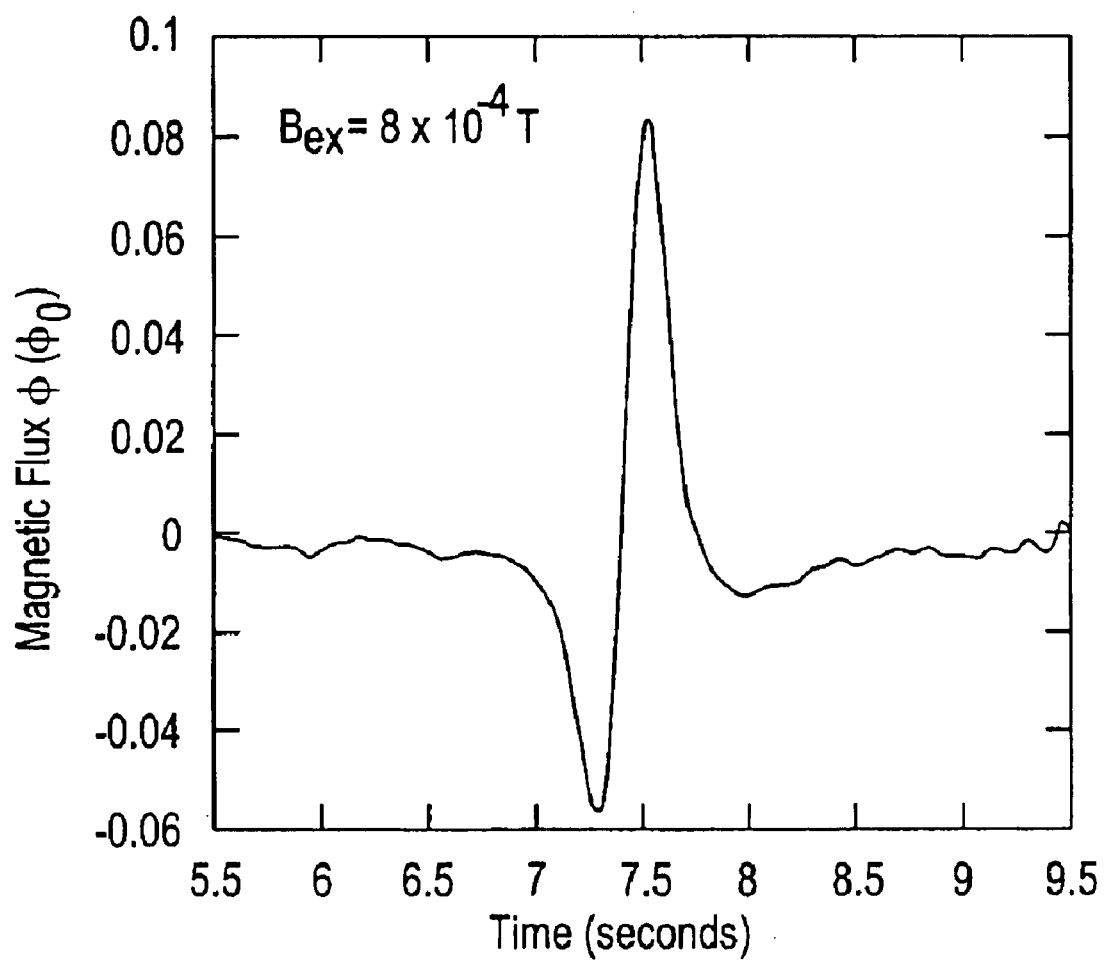
FIG. 4 is a graph showing an output signal of the SQUID.

As shown in the FIG. 4, extremely clear variation of the magnetic field was recorded. Sensitivity of SQUID depends on the distance between a SQUID and an analyte. Therefore, the sensitivity of the apparatus can be regulated by the distance.

EXAMPLE 2

Figure 5:
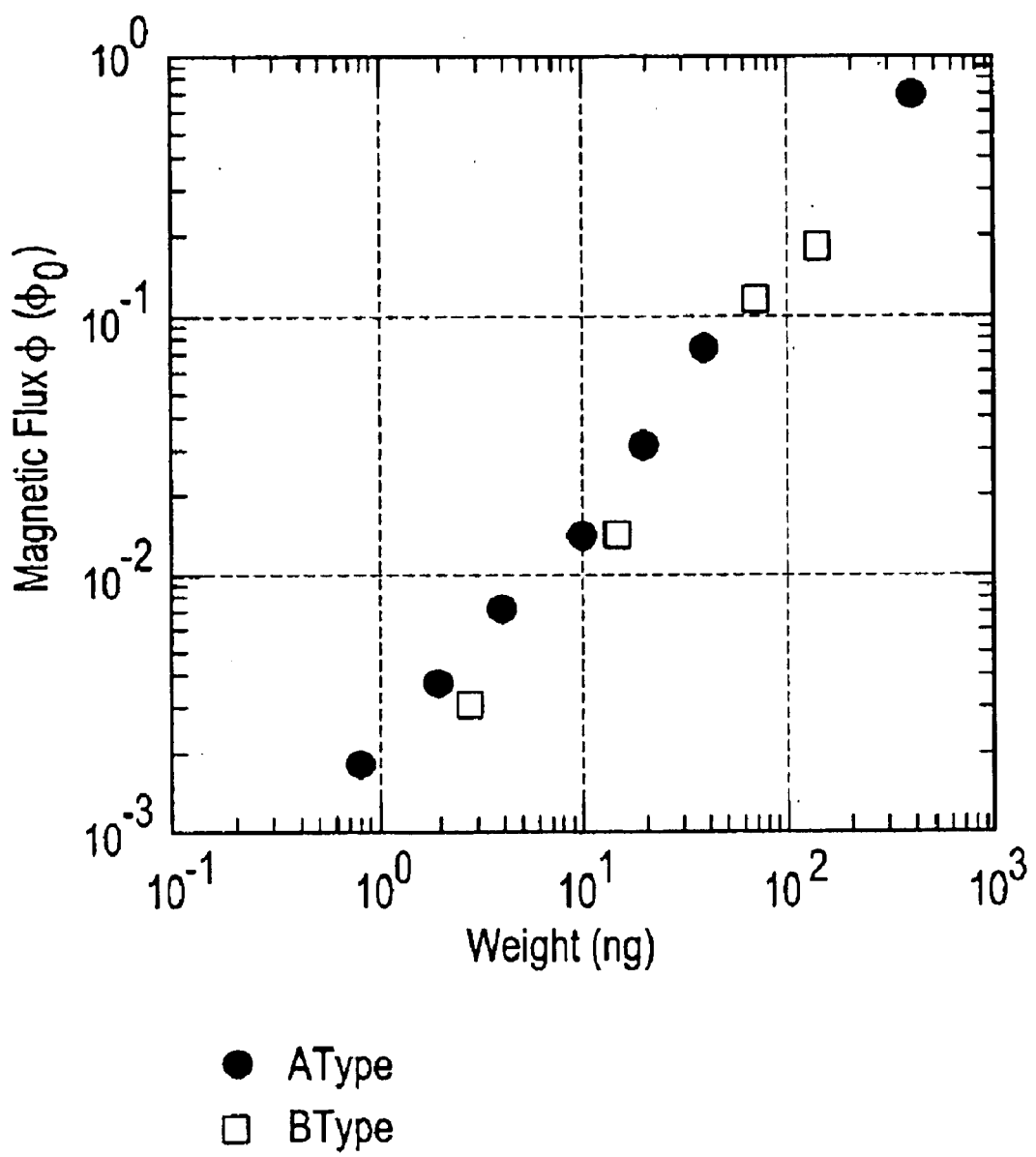
FIG. 5 is a graph showing a relationship between concentration of an antibody and the output of the SQUID.

A relation between the concentration and the detection resultant of the sample is shown in FIG. 5.

Circles plotted in the FIG. 5 show determination resultant of the sample that was labeled with the A type antibody and diluted with PBS in various concentrations. Rectangles plotted in the FIG. 5 show determination resultant of the sample that was labeled with the B type antibody and diluted with PBS in various concentrations. The sample was rat/anti mouse Ig Gl and diluted with PBS. As shown in the FIG. 5, high correlation between the detected magnetic signals and the quantity of the labeled antibody can be seen for the both cases.

EXAMPLE 3

Figure 6:
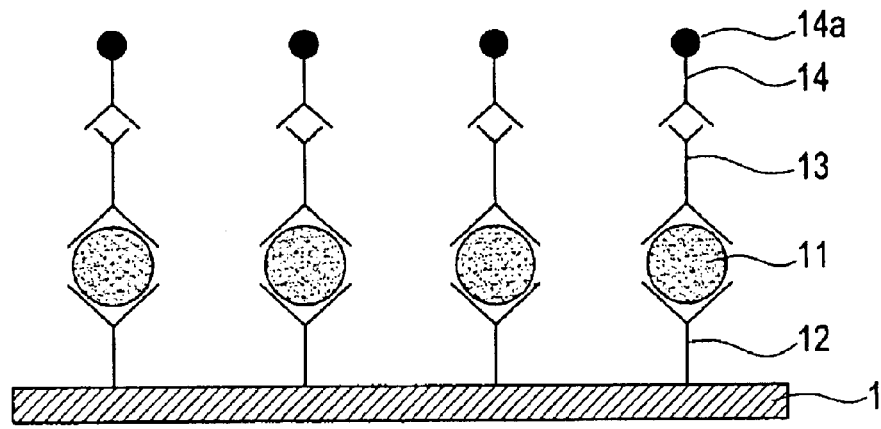
FIG. 6 shows the antigen-antibody reaction labeled with a magnetic label.

Another Sample was prepared. As shown in FIG. 6, in this sample, antigen 11 is fixed by a first antibody 12 to the support 1. Then, a second antibody 13 sticks selectively to the antigen 11. Furthermore, a third antibody 14 labeled with magnetic material 14a sticks to the second antibody 13. The SQUID detects the magnetic material 14a.

The sample put on the region having a diameter of 8 mm on the support. At first, we fixed a "mouse/anti humans interferon βmonoclonal antibody (YMASA company, JAPAN) as the first antibody 12 in region. Next, we let a humans-interferon B as the antigen 11 react to the region at 37 degrees Centigrade for 3 hours. Then we prepared a rabbit-anti human interferon μ/polyclonal antibody (Bio-Rad company, U.S.A.) as second antibody 13 and goat/anti rabbit ig G as the third antibody 14. The Goat/anti rabbit Ig G has been labeled with a magnetic material ultrafine particle and was reacted to the region at 37 degrees Centigrade for 1 hours.

Figure 7:
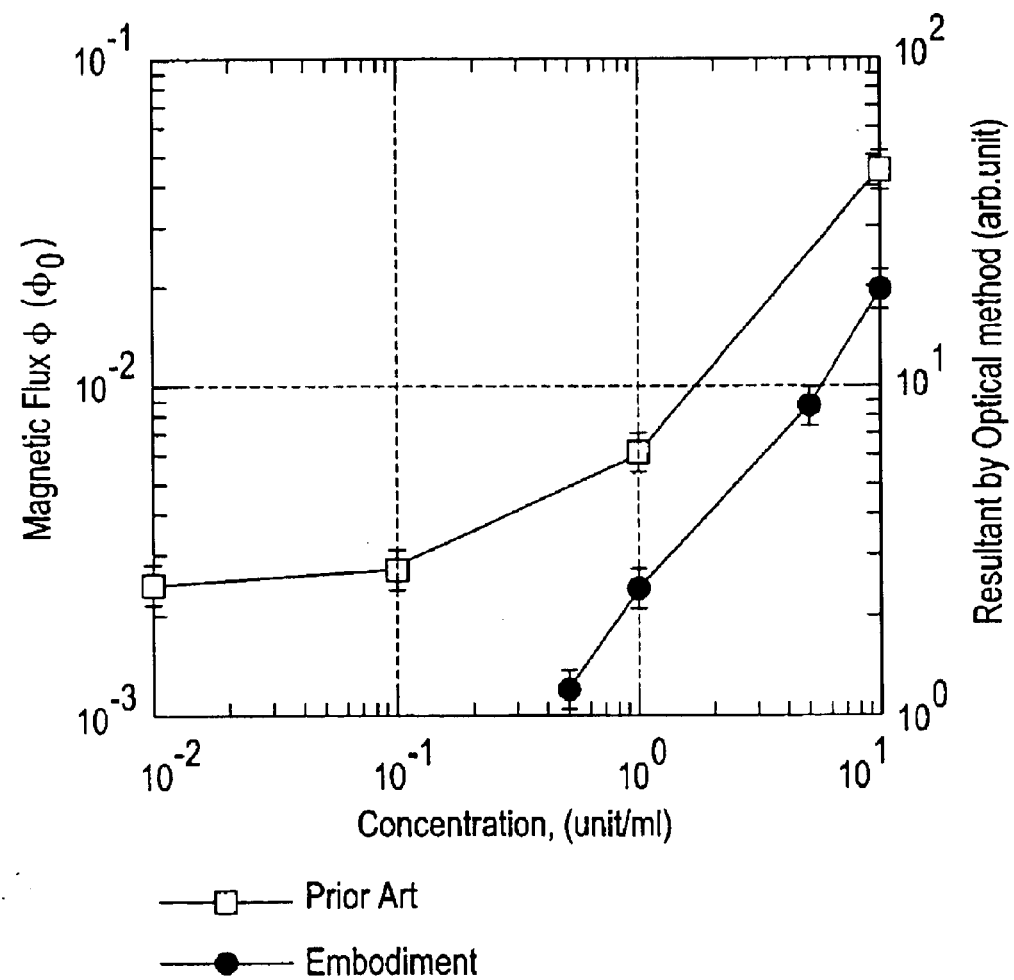
FIG. 7 is a graph showing measured resultant in comparison with a resultant by a prior art.

Determination effect by measuring the sample above is shown in FIG. 7. The determination resultant is plotted with circles. At the same time, rectangles are plotted in the FIG. 7. These rectangles means resultant surveyed by an optical method according to a prior art, ELISA system type II by Biotrak company. In this method, at first, an antibody is reacted to an antigen and next, a stroma is added them. Then the coloring antibody can be detected. For reference, the same goat/anti rabbit Ig G was used as an antibody.

As shown in the FIG. 7, this optical method shows good correlation with specified field where the concentration is more than 1 unit/ml. However, the correlation becomes worsen with lower field than the specified field. On the contrary, a good correlation is maintained by the method of the present invention. Then we understood the method of the present invention is clearly superior to the prior art. As explained, the method of the present invention can realize high sensitivity and high accuracy. Furthermore, a magnetic material can be smaller than 600 pg, therefore, the sensitivity of the present invention should be improved easily.

What is claimed is:

1. A method for immunoassay with a magnetic material label, the method comprising:
   (1) preparing an analyte labeled with said magnetic material label;
   (2) applying said analyte labeled with said magnetic material label, to an antigen fixed to a support so that said analyte is bounded to said antigen by means of an antibody/antigen reaction;
   (3) magnetizing said magnetic material label on said analyte bounded to said antigen, by a magnetic field, thereby forming a magnetized magnetic material labeled analyte; and
   (4) while continuing to apply said magnetic field which magnetizes the magnetic material label, detecting the magnetized magnetic material labeled analyte by sensing, by using a Superconducting Quantum Interference Device, a magnetic flux component which is generated from said magnetized magnetic material labeled analyte and which is at a right angle to the direction of said magnetic field which magnetizes said magnetic material label.

2. A method claimed in claim 1, wherein said magnetic field which magnetizes said magnetic material label is a static magnetic field.

3. A method claimed in claim 1, wherein said Superconducting Quantum Interference Device detects variation of the strength of said magnetic flux component which is generated from said magnetized magnetic labeled analyte and which is at the right angle to the direction of said magnetic field which magnetizes said magnetic material label, by moving said magnetized magnetic material labeled analyte through said magnetic field which magnetizes said magnetic material label.

4. A method claimed in claim 1, wherein said magnetized magnetic material labeled analyte moves in parallel to said magnetic field which magnetizes said magnetic material label.

5. A method claimed in claim 1, wherein said step (4) is performed by moving said support through said magnetic field which magnetizes said magnetic material label so that said magnetized magnetic material labeled analyte passes within a detection region of said Superconducting Quantum Interference Device.

6. A method claimed in claim 5, wherein a portion of said support has a sufficient length so that in the course of moving said support through said magnetic field which magnetizes said magnetic material label, a portion of said support exists within said detection region of said Superconducting Quantum Interference Device without said magnetized magnetic material labeled analyte.

7. A method for immunoassay with a magnetic material label the method comprising:
   (a) preparing an analyte labeled with said magnetic material label;
   (b) applying said analyte labeled with said magnetic material label, to an antigen fixed to a support so that said analyte is bounded to said antigen by means of an antibody/antigen reaction;
   (c) magnetizing said magnetic material label on said analyte bounded to said antigen, by a first magnetic field along a first direction, thereby forming a magnetized magnetic material labeled analyte; and
   (d) while continuing to apply said magnetic field which magnetizes the magnetic material label, and while moving said magnetized magnetic material labeled analyte in said first direction, detecting the magnetized magnetic material labeled analyte by sensing, by using a use of Superconducting Quantum Interference Device, a variation of the strength of a magnetic flux component generated from the magnetized magnetic material labeled analyte, along a second direction perpendicular to said first direction.

8. A method claimed in claim 7, wherein said magnetic field which magnetizes said magnetic material label is a static magnetic field.

9. A method claimed in claim 7, wherein said step (d) is performed by moving said support in said first direction through said magnetic field which magnetizes said magnetic material label.

10. A method claimed in claim 7, wherein said step (d) is performed by moving said support through said magnetic field which magnetizes said magnetic material label so that said magnetized magnetic material labeled analyte passes within a detection region of said Superconducting Quantum Interference Device.

11. A method claimed in claim 10, wherein a portion of said support has a sufficient length so that in the course of moving said support through said magnetic field which magnetizes said magnetic material label, a portion of said support exists within said detection region of said Superconducting Quantum Interference Device without said magnetized magnetic material labeled analyte.

* * * * *